United States Patent [19]

Mills et al.

[11] Patent Number: 4,940,803
[45] Date of Patent: Jul. 10, 1990

[54] PROCESS FOR SYNTHESIS OF 1R,2R,5R-2-HYDROXY-6-OXO-7-OXABICYCLO[3.2.1]-OCTANE

[75] Inventors: Sander G. Mills, Woodbridge; Ralph P. Volante, East Windsor; Ichiro Shinkai, Westfield, all of N.J.

[73] Assignee: Merck & Co., Inc., Rahway, N.J.

[21] Appl. No.: 197,551

[22] Filed: May 23, 1988

[51] Int. Cl.$^5$ .............................................. C07D 307/77
[52] U.S. Cl. ................................. 549/302; 204/157.6; 204/157.63
[58] Field of Search ..................... 549/302; 204/157.6, 204/157.63

[56] References Cited

PUBLICATIONS

S. Mills et al., *Tetrahedron Letters*, 29, No. 3, 281 (1988).
M. Philippe et al., *J. Antibiotics*, 35, 1507 (1982).
W. P. Neumann, 665, *Synthesis* (1986).

*Primary Examiner*—Jane T. Fan
*Attorney, Agent, or Firm*—Robert J. North; Melvin Winokur; Charles M. Caruso

[57] ABSTRACT

A process is described for the synthesis of hydroxy lactone 3, being 1R, 2R, 5R-2-hydroxy-6-oxo-7-oxabicyclo[3.2.1]-octane, in optically pure form, which is useful as an intermediate in the synthesis of the $C_{20}$–$C_{34}$ chain of the macrolide structure for the immunosuppressant FK-506. This compound is also useful as a precursor for producing an ultraviolet radiation absorber.

7 Claims, No Drawings

PROCESS FOR SYNTHESIS OF 1R,2R,5R-2-HYDROXY-6-OXO-7-OXABICYCLO[3.2.1]-OCTANE

BACKGROUND OF THE INVENTION (1) Field of the Invention

This invention relates to a process for producing hydroxy lactone 3: 1R, 2R, 5R-2-hydroxy-6-oxo-7-oxabicyclo[3.2.1]-octane, in optically pure form, useful as a precursor for producing an ultraviolet radiation absorber and as an intermediate in synthesizing the $C_{20}$-$C_{34}$ fragment of the immunoregulant FK-506 and analogs thereof.

(2) Brief Disclosures in the Art

The novel 23-membered tricyclo-macrolide FK-506 very recently isolated and characterized by Tanaka, Kuroda, and co-workers, see JACS, 109, pp. 5031, 1987, and EPO Publication No. 0,184,162, has been shown to possess exceptional immunosuppressive activity. The potential usefulness of such an agent in bone marrow and organ transplantations coupled with its unique structural features has prompted many in the field to initiate an effort towards the total synthesis of FK-506. A highly diastereoselective synthesis of a C.20-C.34 subunit A, in its correct absolute configuration, i.e.,

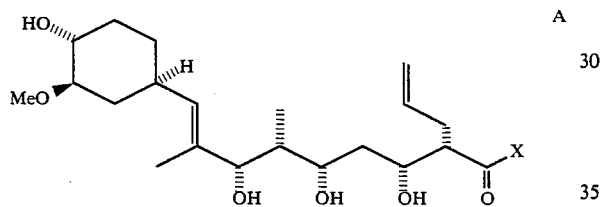

has already been achieved as reported by S. Mills, R. Desmond, R. A. Reamer, R. P. Volante and I. Shinkai in *Tetrahedron Letters,* 1988, 29, 281.

In the course of that work, the need was established for the optically pure form of 1R, 2R, 5R-2-hydroxy-6-oxo-7-oxabicyclo[3.2.1]-octane of the structure:

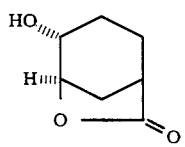

Although the racemic form was known (see the reference of Tanaka, H.; et al, *J. Am. Chem. Soc.,* 1987, 109, 5031; also Grewe, R.; Heinke, A.; Sommer, C.; *Chem Ber.,* 1956, 89, 1978–1988), no procedure for obtaining optically pure 3 was described.

What is needed is an overall general synthesis utilizing readily available starting materials which would allow the synthesis of the hydroxy lactone 3, 1R, 2R, 5R-2-hydroxy-6-oxo-7-oxabicyclo[3.2.1]-octane in its desired optically pure form.

SUMMARY OF THE INVENTION

It has been found that by treating quinic acid lactone 1 with about 3 equivalents of thiocarbonyldiimidazole (TCDI) in refluxing dry 1,2-dichloroethane under nitrogen atmosphere, good yields of the dithiocarbonyl compound 2 can be achieved. The dithiocarbonyl compound 2 can surprisingly be selectively bis-deoxygenated by treatment with tri-n-butyltin hydride and azobisisobutyronitrile in refluxing dry xylenes under a nitrogen atmosphere to obtain good yields of optically active 3 in high purity. This is in contrast to the prior art (see above-described reference of Tanaka, et al.) which only produces the racemic form.

In accordance with the present invention there is provided a process comprising the steps of:

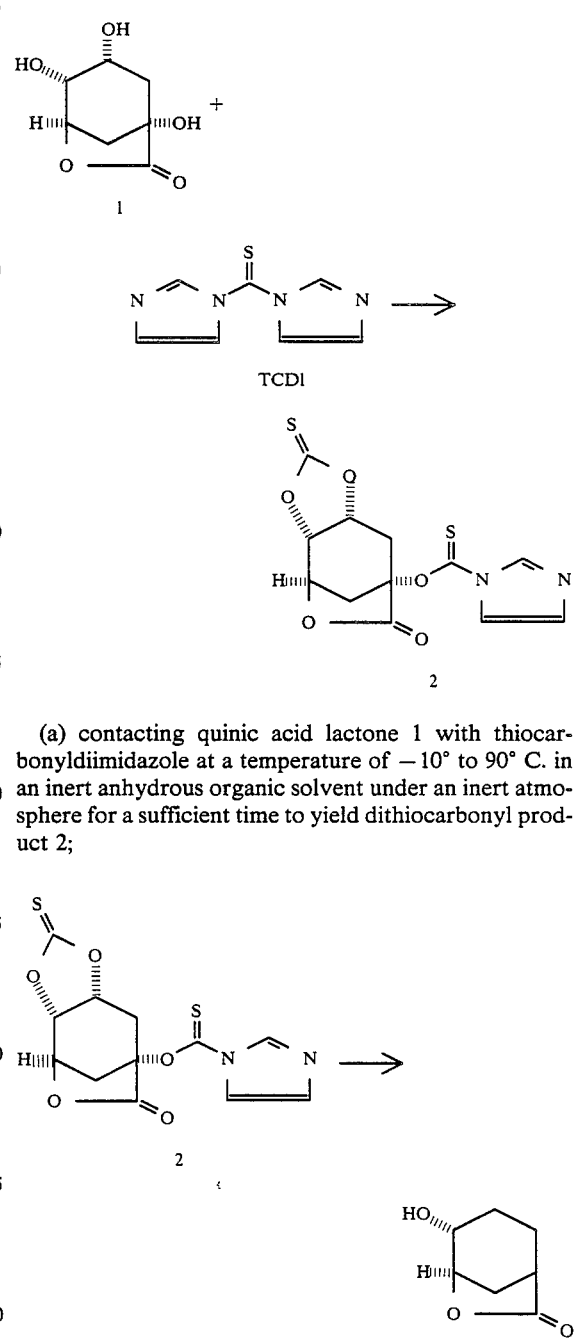

(a) contacting quinic acid lactone 1 with thiocarbonyldiimidazole at a temperature of −10° to 90° C. in an inert anhydrous organic solvent under an inert atmosphere for a sufficient time to yield dithiocarbonyl product 2;

(b) contacting product 2 from step (a) with a trihydrocarbyltin hydride, an azobisalkylnitrile in an inert atmosphere, for a sufficient time to form 3. This lactone 3 is useful as a precursor for producing an ultraviolet radiation absorber of the formula

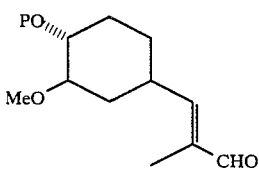

as described in Examples 3-7 wherein P is a triorganosilyl protecting group.

DETAILED DESCRIPTION OF THE INVENTION AND PREFERRED EMBODIMENTS

The process of the present invention can be readily understood by reference to the following Flow Chart A.

FLOW CHART A

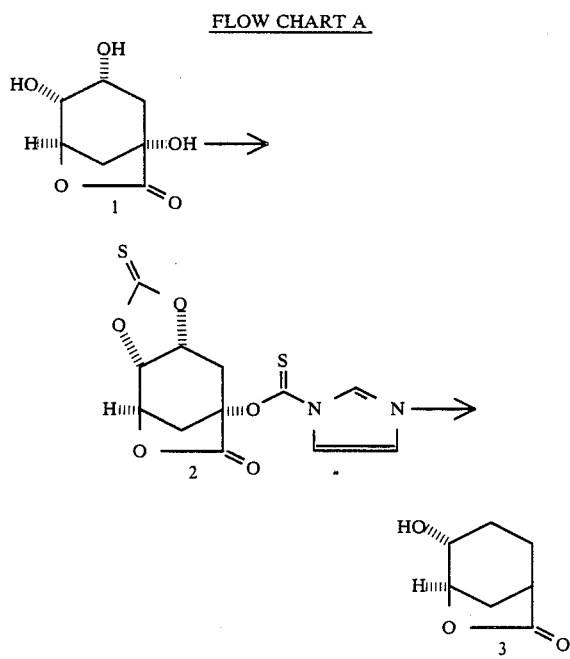

In this flow scheme, the starting material 1, quinic acid lactone, is prepared by lactonization of the readily available commercial product 1R, 3R, 4R, 5R-quinic acid, by the below-described procedure of Philippe et al, in Example 1, hereby incorporated by reference.

The quinic acid lactone 1 is reacted with thiocarbonyldiimidazole (TCDI) (commercially available) in a molar ratio of TCDI/1 of about 2:1 to 5:1 and preferably 3:1.

The solvent used is an inert organic solvent for both 1 and TCDI, being anhydrous, and having a boiling point of about 16° to 120° C.

Representative examples of said inert, anhydrous organic solvent include, e.g. $C_5$ to $C_{12}$ cyclic or acyclic hydrocarbons including hexane, cyclohexane, benzene, toluene, xylenes, and the like, and a halogenated alkane, e.g. $C_1$ to $C_6$, containing 1 to 6 halogens including chlorine, flourine. Representative examples are chloroform, carbon tetrachloride, methylenechloride, chlorobenzene, tetrachloroethane, and dichloroethane.

Concentrations of 1 in the solvent are in the range of 0.05M to 0.5M, and preferably 0.2M.

The mixture is heated, preferably at reflux at 50° to 100° C., for a sufficient time to form 2.

Time required for the reaction is generally in the range of 1 to 4 hours. Generally at the above concentrations, a time of 2½ hours is sufficient to result in a substantial yield of 2 which is in the range of about 40 to 80%.

The resulting solid 2 is collected, washed with an organic liquid, being a non-solvent for 2, e.g. methylethylketone and dried. Further solid can be recovered from the reactive liquid, i.e. mother liquor.

The bisdeoxygenation of 2 is conducted by heating with a suitable trihydrocarbyltin hydride, preferably a trialkyltin hydride, e.g. tri-n-butyltin hydride and an azodialkylnitrile, e.g. azobisisobutylnitrile in a suitable dry organic solvent, e.g. xylene, t-butylbenzene, diethylbenzene, and the like.

The trihydrocarbyltin hydride which functions as a source of preferably trialkyltin radicals and a hydrogen radical source can be tri-n-butyltin hydride, triphenyltin hydride, trimethyltin hydride, triethyltin hydride, and the like, and preferably tri-n-butyltin hydride.

The azobisalkylnitrile which functions as a radical initiator, can be azobisisobutyronitrile, light, and the like, and preferably azobisisobutyronitrile (AIBN).

Generally, the reagent trialkyltin hydride is added first in portions to a heated solution of 2 in the xylene. Then, the azonitrile is added with the last portions of tin hydride. Generally, the reaction is conducted in the absence of light to avoid extraneous catalyzed reactions. Generally, the reaction is conducted at a temperature of 80° to 150° C., preferably 125° to 135° C. and is preferred particularly at the reflux temperature of xylene (bp. 138° C.).

After the reagents are added, the reaction mixture is heated and refluxed for 0 to 3 hours and preferably 0.75 hours.

Yields of 3 are generally in the range of 30 to 70%.

Purification of 3 is accomplished conventionally, e.g. by column chromatography.

Conventional apparatus is used for carrying out the process.

The compound is useful as a precursor for producing an ultraviolet absorber described hereinabove, which can be used, for example, by mixing with a pigmented paint to absorb ultraviolet radiation to extend the lightfastness of the color.

The following examples are illustrative of the invention and should not be considered as being limitations on the scope of the instant invention.

EXAMPLE 1

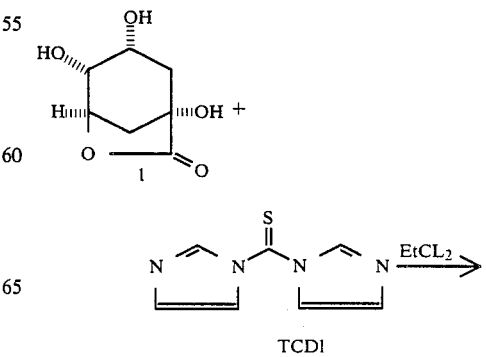

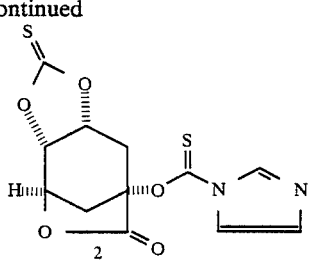

To a suspension of 10.0 g (57.4 mmol) of quinic acid lactone 1 (obtained by the known procedure of Philippe, M.; Sepulchre, A. M.; Gero, S. D.; Loibner, H.; Streicher, W.; Stutz, P. *J. Antibiotics*, 1982, 35, 1507-1512) in 280 mL dry 1,2-dichloroethane was added, in portions, 30.0 g (168.3 mmol) of thiocarbonyldiimidazole (TCDI) at reflux under dry nitrogen. The resulting solution was refluxed in the dark for two more hours, and the mixture was then cooled to room temperature. Solvent was removed under vacuum on a rotary evaporator, and the residual brown paste was treated with 20 mL of a 50:50 (v/v) solution of acetonitrile:methyl ethyl ketone. The resulting suspension was stirred at 0° C. for 20 min, and the solid was then collected by filtration, washing with 5 mL of 1:1 acetonitrile: methyl ethyl ketone and then with methyl ethyl ketone. The resulting light yellow solid 2 was dried in a stream of nitrogen in the filter funnel, and the dried solid was then washed with 20 mL of methyl ethyl ketone in a stream of nitrogen, to give 10.70 g of a light yellow powder. The combined mother liquors were concentrated and chromatographed rapidly on 178 g of silica with ethyl acetate as eluant. The relevant fractions were concentrated in vacuo, and the residue was taken up in 40 mL of boiling toluene, and the resulting suspension was placed in a freezer overnight. The solid was collected to give an addition 3.24 g of product 2 for a total of 13.94 g (74%).

Analysis: IR (film) 3000, 1810, 1396, 1305, 1290 cm$^{-1}$.

$^1$H NMR (300 MHz, (CD$_3$)$_2$SO, (CH$_3$)$_4$Si) δ 8.50 (d,1H,J=0.8), 7.80 (d,1H,J=1.4), 7.08 (d,1H,J=1.1), 5.65 (td,1H,J=8.1,2.7), 5.34 (app t,2H,J=8), 3.82 (dd,1H,J=12.6,6.1), 3.03 (dd,1H,J=15.3,2.8), 2.82 (ddd,1H,J=15.2,8.2,2.4), 2.41 (d,1H,J=12.7).

TLC - R$_f$=0.45 (80:20 ethyl acetate:hexanes)

EXAMPLE 2

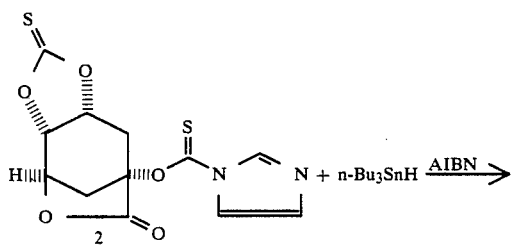

To a solution of 1.00 g (3.06 mmol) of the dithiocarbonyl compound 2 in 100 mL dry xylenes at reflux under a dry nitrogen atmosphere was added 0.62 mL (2.30 mmol) of tri-n-butyltin hydride. After 20 min, 0.62 mL more tri-n-butyltin hydride was added. After 50 min total, 1.65 mL (6.12 mmol) tri-n-butyltin hydride and ca. 2 mg azobisisobutylnitrile was added. After 75 min more, the mixture was allowed to cool to room temperature and was concentrated under high vacuum. The residue was taken up in a warm mixture of 100 mL acetonitrile and 80 mL hexanes. The layers were separated, and the lower (acetonitrile) layer was washed once with 60 mL of hexanes. The acetonitrile layer was concentrated in vacuo to 0.55 g of an oil, which was chromatographed on 29 g silica with 3:1 (v:v) ethyl acetate: hexanes. Pooling of the relevant fractions gave 184 mg (43%) of a white solid 3 which by $^1$H NMR was about 95% pure.

Analysis: IR (CHCl$_3$) 3600, 3450, 3010, 2980, 2950, 1775, 1155, 1070, 1030, 1010 cm$^{-1}$.

$^1$H NMR (300 MHz, CDCl$_3$, (CH$_3$)$_4$Si) δ 4.68 (t,1H,J=5.2), 4.19 (d,1H,J=3), 2.62 (m,1H), 2.40 (d,1H,J=11.9), 2.21 (m,1H), 2.04 (d,1H,J=3.7), 2.0–1.7 (m,4H).

TLC - R$_f$=0.22 (50:50 hexanes:ethyl acetate)

EXAMPLE 3

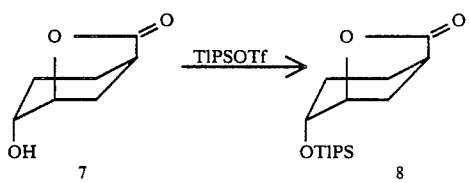

To a solution of 80.1 g (0.563 mol) of the hydroxylactone 7 in 560 mL of dry methylene chloride under nitrogen was added 131 mL (1.125 mol) of 2,6-lutidine. The resulting mixture was cooled to 0° C. and treated dropwise over 30 minutes with 151 mL (0.563 mol) of triisopropylsilyl triflate (TIPSOTF). The reaction was then warmed to room temperature and stirred for 2 hours. The reaction mixture was transferred to a separating funnel containing 2 L of hexanes and washed with 500 mL cold 5% HCl. The organic layer was washed 2 times with 500 mL H$_2$O, and 500 mL brine. The organic layer was dried over sodium sulfate and concentrated in vacuo to yield 166.4 g (98.9% crude yield) of the TIPS lactone 8 as a yellow oil. The crude product was used without further purification in the subsequent reaction.

$^1$H NMR (300 MHz, CDCl$_3$, (CH$_3$)$_4$Si): δ 4.60 (t, 1H, J=5.3), 4.20 (m 1H), 2.58 (m, 1H), 2.45 (d, 1H, J=11.6), 2.22–2.12 (m, 1H), 1.92–1,73 (m, 4H), 1.07 (s, 1H).

EXAMPLE 4

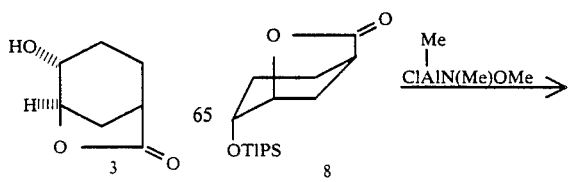

-continued

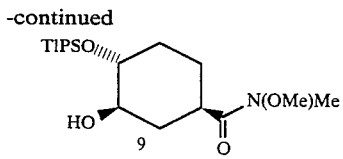

Preparation of Weinreb's Aluminum N-methoxyamide Reagent

To a 0° C. suspension of 117 g (1.13 mol) of N,O-Dimethylhydroxylamine hydrochloride in 650 mL of dry toluene under nitrogen was added dropwise 565 mL (1.13 mol) of a 2 M trimethylaluminum/toluene solution. The resulting mixture was warmed to room temperature, stirred 1 hour and the resulting clear, colorless solution was cooled to −20° C. To this solution of the aluminum N-methoxy N-methyl amide was added dropwise a solution of 166.4 g (0.557 mol) of the TIPS-protected lactone 8 in 500 mL of dry tetrahydrofuran. The resulting mixture was warmed to room temperature and stirred for 3 hours. The reaction was transferred via cannula into 1 L of an ice cold, stirred solution of 5% HCl, then the mixture was extracted with 2 L of ethyl acetate. The ethyl acetate was washed with 2 L of H$_2$O, 500 mL of brine, dried over magnesium sulfate and concentrated in vacuo to 500 mL to give a thick slurry. After an overnight age at 0° C., the product was collected by filtration, the cake was washed with cold hexanes and air dried to yield 147.2 g of a white solid, mp. 89–92° C. A second crop yielded 15.7 g for a total yield of 162.9 g of 9 (81.3%). The $^1$H NMR was consistent with desired product. $^1$H NMR (300 MHz, CDCl$_3$, (CH$_3$)$_4$Si), δ 3.70 (s,3H), 3.67–3.60 (m, 1H), 3.53–3.46 (m, 1H), 3.35 (m, 1H), 3.19 (s, 3H), 2.88 (m, 1H), 2.13–1.95 (m, 2H) 1.89–1.79 (m, 1H), 1.68–1.36 (m,3H), 1.08 (s, 21H). $^{13}$C NMR (300 MHz, CDCl$_3$): δ 176.0, 75.4, 73.5, 61.3, 36.9, 32.4, 30.7, 25.6, 18.0, 17.9, 12.4.

IR(CHCl$_3$) 2940, 2865, 1640, 1460, 1380, 1200, 1110, 1070 cm$^{-1}$.

EXAMPLE 5

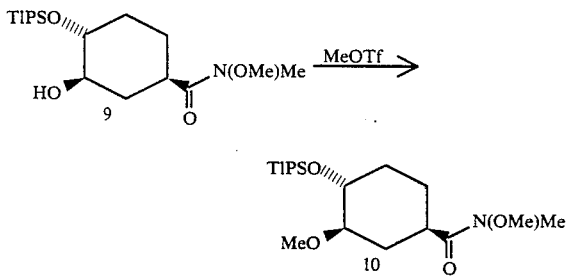

To a solution of 195.1 g (0.95 mol) of 2,6-di-t-butyl-4-methylpyridine in 1 L of dry methylene chloride under nitrogen was added 100 g (0.61 mol) of methyl trifluoromethanesulfonate. The resulting mixture was stirred at room temperature for 2 hours. A solution of 154.7 g (0.43 mol) of the hydroxyamide 9 in 750 ml of dry methylene chloride was then added to the pyridine-methyltriflate solution via cannula at room temperature and the resulting mixture was stirred for 31.5 hours. Analysis via HPLC showed the reaction to be 99.5% complete. The reaction was quenched with 50 mL of MeOH and the resulting mixture was stirred for 5 hours at room temperature. The reaction was concentrated in vacuo with stirring to a volume of 500 mL, and then diluted with 800 mL hexanes. The solid was removed by filtration and the cake was washed with two 500 mL portions of methylene chloride. The filtrate was washed with three 500 mL portions of 10% HCl and with 500 mL H$_2$O. The combined aqueous washes were extracted with one 500 mL portion of hexanes. The combined organic layer was washed with 500 mL of 3% NaHCO$_3$, dried over sodium sulfate and concentrated in vacuo to yield 162.5 g (101% crude yield) of product 10 as a pale yellow oil. Analysis via $^1$H NMR and LC were consistent with desired product. $^1$H NMR (300 MHz, CDCl$_3$, (CH$_3$)$_4$Si): δ 3.70 (s, 3H), 3.60 (m, 1H), 3.37 (s, 3H), 3.17 (s, 3H), 3.00 (m, 1H), 2.71 (app t, 1H), 2.17 (app dg, 1H), 2.01 (m, 1H), 1.73 (m, 1H), 1.67–1.27 (m, 3H), 1.07 (s, 21H). $^{13}$C NMR (75 MHz, CDCl$_3$, (CH$_3$)$_4$Si): δ 175.5, 84.1, 74.4, 61.3, 57.0, 37.7, 33.7, 32.0, 31.9, 26.8, 17.9 17.8, 12.8, 12.6, 12.4, 12.0.

IR (film) 2950, 2870, 1670, 1465, 1110 cm$^{-1}$.

EXAMPLE 6

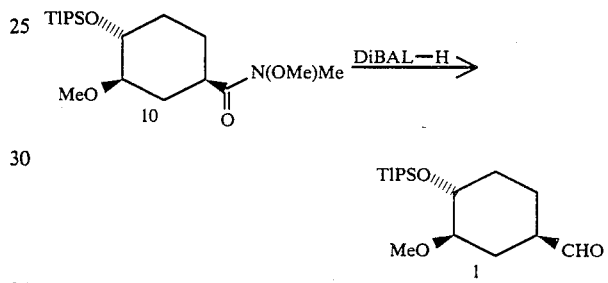

To a −78° C. solution of 100.0 g (0.268 mol) of the amide 10 in 1075 mL of dry tetrahydrofuran under nitrogen was added dropwise 196 mL (0.294 mol) of a 1.5 M diisobutylaluminum hydride/toluene solution. The resulting mixture was stirred for 1.5 hours at −78° C. and transferred via cannula into a stirred mixture of 1 L 10% HCl, ice, and 1 L hexanes. The mixture was transferred to a separatory funnel, the layers were separated and the aqueous layer was extracted with two 1 L portions of ethyl acetate. The combined organic layers were dried over sodium sulfate, filtered through a thin pad of celite and concentrated in vacuo to yield 79.8 g (94.8% crude yield) of the aldehyde 1 as a clear yellow oil. $^1$H NMR (300 MHz, CDCl$_3$, Me$_4$Si): δ 9.67 (s, 1H), 3.76 (m, 1H), 3.35 (s, 3H), 3.16 (m, 1H), 2.3–2.2 (m, 2H), 2.0–1.85 (m, 2H), 1.8–1.55 (m, 2H), 1.44 (m, 1H), 1.07 (s, 21H). $^{13}$C NMR (75 MHz, CDCl$_3$, Me$_4$Si): δ 203.8, 81.2, 70.8, 57.0, 46.1, 29.0, 26.9, 20.7, 18.0, 12.3.

IR (film) 2950, 2870, 1725, 1460, 1110 cm$^{-1}$.

EXAMPLE 7

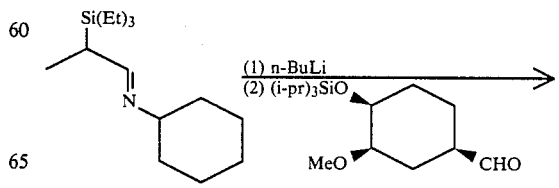

-continued

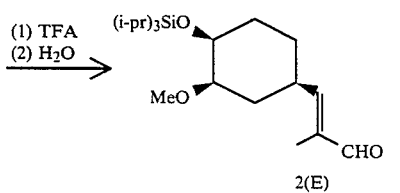

2(E)

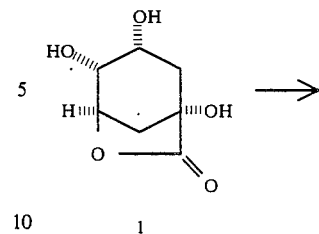

1

Unsaturated Aldehyde 2:

To a −78° solution of 0.366 g (1.44 mmol) of the imine 6 in 2 mL of THF under nitrogen was added 1.02 mL (1.33 mmol) of a 1.3M sec-butyllithium/cyclohexane solution dropwise. The reaction was stirred at −78° C. for 30 min and then was treated with 0.349 g (1.11 mmol) of the aldehyde 1 in 1 mL of THF. The mixture was warmed to −20° C. and was stirred for 1 h. The reaction was quenched with 2 mL of water, and the resulting mixture was extracted with 2×20 mL of ethyl acetate. The combined organic extracts were washed with brine, dried with magnesium sulfate, and concentrated in vacuo. The trifluoroacetic acid isomerization procedure was conducted by dissolving the residue in 5 mL of THF and treating the solution at 0° C. with 0.10 mL (1.323 mmol) of trifluoroacetic acid dropwise under nitrogen. After one hour at 0° C. 2 mL of water were added, and the mixture was stirred at 0° C. for 12 hours. The reaction was poured into a saturated aqueous sodium bicarbonate solution and was extracted with 25 mL of ethyl acetate. The organic phase was washed with brine, dried over magnesium sulfate, and concentrated in vacuo. The residue was purified by flash chromatography with 7% ethyl acetate/hexanes to give 0.329 g (84%) of the unsaturated aldehyde 2(E). Chemical name: E-2-methyl-3- 1R,3R,4R-(3'-methoxy-4'-triisopropylsilyloxy-1'-cyclohexyl) propenal. $^1$H NMR (300 MHz, CDCl$_3$, (CH$_3$)$_4$Si): δ 9.38 (s, 1H), δ 6.31 (d, 1H, J=9.5), δ 3.65 (m, 1H), δ 3.39 (s, 3H), δ 3.06 (m, 1H), δ 2.60 (m, 1H), δ 2.12–1.97 (m, 2H), δ 1.77 (s, 3H), δ 1.76–1.11 (m, 4H), δ 1.08 (s, 21H). $^{13}$C NMR (300 MHz, CDCl$_3$): δ 195.5, 157.4, 137.9, 83.6, 74.1, 57.5, 35.8, 34.3, 33.1, 29.2, 18.1, 12.6, 9.3.

IR (film) 2935, 2865, 1690, 1640, 1455, 1380, 1140, 1110, 1080 cm$^{-1}$.

What is claimed is:

1. A process comprising the steps of:

(a) contacting quinic acid lactone 1 with thiocarbonyldiimidazole at a temperature of 70° to 80° C. in an inert anhydrous organic solvent under an inert atmosphere for a sufficient time to yield dithiocarbonyl product 2;

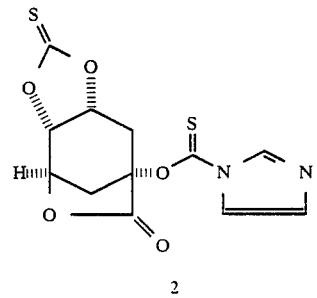

2

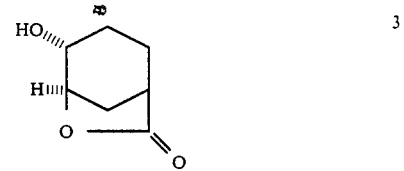

3

(b) contacting product 2 from step (a) with a trihydrocarbyl hydride, an azobisalkylnitrile in an inert anhydrous organic solvent at a temperature of 125° to 140° C., under an inert atmosphere, for a sufficient time to form 3.

2. The process of claim 1 wherein said temperature in step (a) is 70° to 80° C.

3. The process of claim 1 wherein said temperature in step (b) is 125° to 140° C.

4. The process of claim 1 wherein said solvent in step (a) is 1,2-dichloroethane.

5. The process of claim 1 wherein said solvent in step (b) is mixed xylenes.

6. The process of claim 1 wherein said trialkyltin hydride in step (b) is tri-n-butyltinhydride.

7. The process of claim 1 wherein said azobisalkylnitrile in step (b) is 2,2'-azo-bis-[2-methylpropionitrile].

* * * * *